United States Patent [19]

Casey et al.

[11] Patent Number: 4,593,130

[45] Date of Patent: Jun. 3, 1986

[54] SYNTHESIS OF 10-HYDROXYMETHYL-9-ANTHRALDEHYDE

[75] Inventors: Donald J. Casey, Ridgefield, Conn.; William J. Trzaskos, Belcamp, Md.

[73] Assignee: American Cyanamid Company, Stamford, Conn.

[21] Appl. No.: 748,287

[22] Filed: Jun. 24, 1985

[51] Int. Cl.$^4$ ............................................ C07C 45/58
[52] U.S. Cl. ................................................ 568/427
[58] Field of Search ...................... 568/427, 450, 431

[56] References Cited

U.S. PATENT DOCUMENTS 2,694,090 11/1954 Wild et al. ............................ 568/450
3,505,406 4/1970 Wendler ............................... 568/427
4,495,371 1/1985 Neri et al. ............................ 568/427

*Primary Examiner*—Bernard Helfin
*Attorney, Agent, or Firm*—Edward A. Conroy, Jr.

[57] ABSTRACT

This disclosure describes the catalyzed rearrangement of trans-dispiro (oxirane-2,9-(10'H)-anthracene)-10',2''-oxirane to 10-hydroxymethyl-9-anthraldehyde.

4 Claims, No Drawings

SYNTHESIS OF 10-HYDROXYMETHYL-9-ANTHRALDEHYDE

BRIEF SUMMARY OF THE INVENTION

This invention is concerned with a novel process for the preparation of 10-hydroxymethyl-9-anthraldehyde (II) by the use of supported acidic reagents to effect the epoxide rearrangement of trans-dispiro (oxirane-2,9-(10'H)-anthracene)-10',2"-oxirane (I) as set forth in the following reaction scheme.

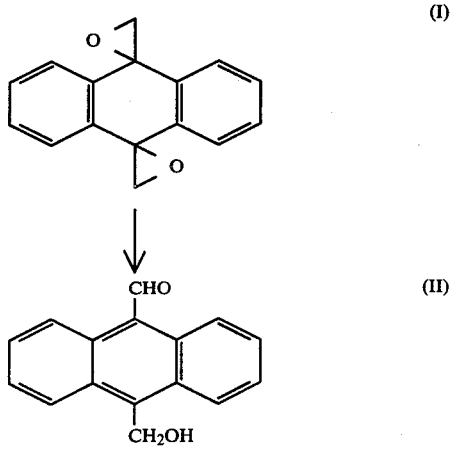

Heretofore, the conversion of (I) to (II) has been accomplished with lithium bromide or boron trifluoride-etherate as reagents for the epoxide rearrangement. Although both of these prior art reagents provide excellent yields of (II), they also present serious waste disposal problems.

DETAILED DESCRIPTION OF THE INVENTION

It has now been discovered that the epoxide rearrangement of (I) to (II) may be effected by the use of supported acidic reagents such as acidic ion exchange resins. Typical acidic ion exchange resins which may be employed in the novel process of the present invention are DOWEX 50 ®, AMERLITE IR120 ®, DOWEX 50W ®, and the like. The reaction is preferably carried out in an inert organic solvent such as tetrahydrofuran, dimethoxyethane, dioxane, dimethylformamide, and the like at temperatures of from about 50° C. to about 100° C. for a period of time sufficient for a substantial degree of rearrangement to occur. This is generally from about 12 to 24 hours. The 10-hydroxymethyl-9-anthraldehyde can be readily oxidized to anthracene-9,10-dialdehyde which is an intermediate for the preparation of anti-cancer agents.

The novel process of the present invention not only provides high yields of (II) from (I) but the synthetic procedure is also greatly simplified. Unlike the prior art reagents, the acidic ion exchange resins employed in the present process can be readily recovered from the reaction and then recycled for re-use, thus making them very cost effective. The process is also an environmentally safe method since less waste is generated for disposal.

The invention will be described in greater detail in conjunction with the following specific example.

EXAMPLE I

Five grams of trans-dispiro (oxirane-2,9-(10'H)-anthracene)-10',2"-oxirane in 100 ml. dimethylformamide was charged to a 250 ml. flask. AMERLITE IR120 ®(0.8 g) was added and the reaction mixture was heated with stirring under argon at 70° C. for 16 hours. The warm reaction mixture was then passed through glass wool into 500 ml. of cold water whereupon the product precipitated. The product was removed by filtration and oven dried yielding 4.95 grams (99% yield) of 10-hydroxymethyl-9-anthraldehyde.

We claim:

1. The process of preparing 10-hydroxymethyl-9-anthraldehyde which comprises rearranging trans-dispiro(oxirane-2,9-(10'H)-anthracene)10', 2"-oxirane in the presence of a catalytic amount of an acidic ion exchange resin in an inert organic solvent at from about 50° C. to about 100° C. for a period of time sufficient for the rearrangement of a substantial proportion of the starting material.

2. The process according to claim 1 wherein the acidic ion exchange resin is AMBERLITE IR120 ®.

3. The process according to claim 1 wherein the acidic ion exchange resin is DOWEX 50 ®.

4. The process according to claim 1 wherein the acidic ion exchange resin is DOWEX 50W ®.

* * * * *